United States Patent
Nicolini

(10) Patent No.: US 7,329,003 B2
(45) Date of Patent: Feb. 12, 2008

(54) SYSTEM, APPARATUS AND METHOD FOR ACCOMMODATING OPTHALMIC EXAMINATION ASSEMBLIES TO PATIENTS

(75) Inventor: Angela E. Nicolini, Abiline, TX (US)

(73) Assignee: Occhi Sani, LLC, Abilene, TX (US)

( * ) Notice: Subject to any disclaimer, the term of this patent is extended or adjusted under 35 U.S.C. 154(b) by 442 days.

(21) Appl. No.: 10/988,409

(22) Filed: Nov. 12, 2004

(65) Prior Publication Data

US 2006/0109424 A1    May 25, 2006

(51) Int. Cl.
*A61B 3/02* (2006.01)
(52) U.S. Cl. ............... 351/244; 351/245; 351/246; 108/43; 108/50.14
(58) Field of Classification Search ........ 351/203–206, 351/211, 212, 244, 245, 246; 108/43, 50.14; 5/630–632, 636, 637
See application file for complete search history.

(56) References Cited

U.S. PATENT DOCUMENTS

| | | | |
|---|---|---|---|
| 1,869,700 A * | 8/1932 | Mandaville | 351/245 |
| 2,837,963 A | 6/1958 | Binstead et al. | |
| 3,572,913 A | 3/1971 | Korb et al. | |
| 4,128,317 A | 12/1978 | LeCover | |
| 4,925,508 A * | 5/1990 | Goto et al. | 156/79 |
| 5,000,563 A | 3/1991 | Gisel | |
| 5,098,426 A * | 3/1992 | Sklar et al. | 606/5 |
| 5,195,705 A * | 3/1993 | Kline et al. | 248/118.3 |
| 5,262,806 A | 11/1993 | Szirth | |
| 5,444,504 A | 8/1995 | Kobayashi | |
| 5,907,387 A | 5/1999 | Schwaegerle | |
| 6,045,225 A | 4/2000 | Hosoi | |
| 6,193,374 B1 | 2/2001 | Williams | |
| 6,575,575 B2 | 6/2003 | O'Brien et al. | |
| 6,712,470 B2 * | 3/2004 | O'Brien et al. | 351/245 |

OTHER PUBLICATIONS

Marco—Classical Products: What's New, website: www.marco.com, Nov. 9, 2004, pp. 1,2.

* cited by examiner

*Primary Examiner*—Hung X. Dang
*Assistant Examiner*—Joseph Martinez
(74) *Attorney, Agent, or Firm*—R. Scott Rhoades; Akin Gump Strauss Hauer & Feld

(57) ABSTRACT

The apparatus provides an improved modified slit lamp assembly light source base and vertical support frame assemblies comprising chin and headrest vertical support legs wherein at least a lower portion of the chin rest vertical supports have been modified in at least a substantially widened fashion. The lower portion of the supports is further modified to jut back or bend away from a seated patient and toward the encroaching base of the slit lamp assembly to provide upper body accommodation while at the same time preventing a patient's upper body to encroach the base of the slit lamp. The assembly's chin/head support frame is mounted on a pivotal tabletop having a pivotal connection means, wherein the pivotal tabletop comprises a plurality of cut-out shapes each working in cooperative conjunction with the modified assemblies to accommodate obese, large-breasted patients and patients with degenerative back disorders, as well as obese doctors.

21 Claims, 6 Drawing Sheets

SYSTEM, APPARATUS AND METHOD FOR ACCOMMODATING OPTHALMIC EXAMINATION ASSEMBLIES TO PATIENTS

FIELD OF THE INVENTION

This present invention relates generally to ophthalmic equipment used primarily in ophthalmic clinics to test ocular health characteristics of various patients. In particular, the present invention relates to a system, apparatus, and method for accommodating ophthalmic assemblies to obese, large-breasted, and/or degeneratively-diseased patients for more comprehensive eye examinations.

BACKGROUND

Since introduction and development of ophthalmic equipment, various types of apparatuses employed have ceased to progress in precision and performance. Many of these known instruments utilize stands and other ophthalmic procedures and are typically manually operated units. These stands include external housings and weight counterbalanced arms that are used to support various types of medical instrumentation. Up to the present time it has been very difficult to impossible to employ all apparatuses for all types of patients for effecting adequate and comprehensive examination and treatment of patients which are seated in front of the ophthalmic equipment and specifically in front of slit lamp assemblies mounted to stationary tables.

Many times the tables are mounted to stands that require fine tuning adjustments to position the slit lamp assembly in a desired position that is relative to a seated patient. Often is it necessary for medical professionals to first adjust an arm to allow a patient to be seated properly.

Current ophthalmic equipment and methods used to position and examine patients hampers the efficiency of various medical personnel specifically, optometrists and ophthalmologists. Due to the varying physical attributes of patients, specifically those who are obese and/or large-breasted, it is often very difficult, if not impossible, to properly position the patient in front of current slit lamp assemblies that are mounted to fixed tables.

At times the optometrists or ophthalmologists are forced to forego certain examination techniques and procedures which utilize slit lamp assemblies and other ophthalmic equipment because it is almost impossible to properly position the patient close enough to the assembly to place a patient's chin in the chin rest of the assembly. Moreover, it is impossible for the physician to position the patient close enough to examine their ocular structures without utilizing the chin rest.

These difficulties force optometrists and ophthalmologists to work under limited condition, sometimes without providing the comprehensive care they are trained to do.

There are several devices that accommodate an ophthalmic apparatus during an ophthalmic examination and provide a support means for medical equipment. For example, U.S. Pat. No. 4,128,317 to Lecover discloses a head positioning means, accommodated on a stand used in conjunction with equipment for examinations of the eyes with conventional lower and upper support ledges, comprising a bi-directionally movable chin support mounted on the lower ledge.

U.S. Pat. No. 5,907,387 to Schwaegerle discloses a medical instrument support mechanism, particularly suitable for ophthalmological instruments, including first and second support arms and a suitable base member in which the first arm is vertically pivotal with respect to the base member and the base member is pivotal with respect to another support member, such as a support pole.

Finally, U.S. Pat. No. 5,000,563 to Gisel discloses an apparatus intended for the observation and treatment of a patient, in particular for ophthalmological cases. Such apparatus includes an arrangement for ophthalmological observation and treatment, means for effecting positioning and adjustment of the arrangement, an underframe for supporting the means and the arrangement as well as a head rest system. In this apparatus the means comprises jointed means permitting rotation of the arrangement around a horizontal axis. The apparatus is applied for observing and treating the eyes of a patient who may be seated or recumbent.

These devices provide a suitable means for mounting medical equipment and a means for examining patients. However, these inventions do not provide an ophthalmic assembly for obese and/or large-breasted patients. Although several references disclose various ways of placement of specific instruments, none disclose assemblies for accommodating the obese and/or large-breasted patient. Similarly, none disclose a means to accommodate patients that may be forced to sit in a "hunched-back" posture due to osteoporosis or other degenerative diseases.

What is needed, therefore, is a slit lamp assembly mounted to a tabletop wherein the slit lamp assembly comprises modified vertical chin rest supports for effecting proper positioning of a patient for examination, wherein the tabletop has been modified to easily accommodate large-breasted and/or obese patients. The combination of such modifications would enable the optometrist and/or ophthalmologist to more fully examine the patient than what is presently being done with current assemblies and their associated tabletop mounting. The modifications needed would enable obese and/or large-breasted patients to sit closer to the slit lamp assembly and the examining physician with less effort or strain.

It is, therefore, an objective of the present invention to provide a method and apparatus for examining obese, large-breasted, and/or degeneratively-diseased patients easily, comfortably, and comprehensively during an ophthalmic examination.

It is also desirable to provide a tabletop for mounting the modified slit lamp assembly and other instruments that will allow the tabletop/slit lamp assembly to pivot in a plurality of planes to further accommodate patients suffering from degenerative diseases, wherein such patients are forced to always sit in a hunched over position during an examination. Such modifications are needed to enable the physician to alter the tabletop base and the slit lamp assembly combination simultaneously to allow for examination of these patients.

SUMMARY OF THE INVENTION

The apparatus is a modification of a traditional slit lamp examination assembly, chin and headrest supports, and tabletop assembly. The present invention provides for at least a modified slit lamp assembly light source base and vertical chin rest supports that comprise a chinrest and headrest wherein vertical supports have been modified in a substantially widened fashion and also to jut back and away near a lower portion in an arcuate fashion from a seated patient being examined.

More specifically, a lower portion of the chin rest vertical support bars of the frame jut back toward an adjacent light source base of a slit lamp assembly. Such "jut back" or bending back of the bars causes a significant portion of the once totally vertical bars to be moved further away from the patient when seated. In addition, the vertical bars are positionally widened to allow obese and/or large-breasted patients to be adequately positioned close enough to the examination assembly to allow for comprehensive eye examinations that were not possible prior to the modifications disclosed by the present invention. According to the present invention the bars also prevent the patient's body from contacting the instrument.

The assembly is mounted on a tabletop, wherein the tabletop comprises curvilinear cut-outs in the doctor's and patient's side of the table that works in conjunction with the modified slit lamp assembly to more easily accommodate obese and/or large-breasted patients or doctors. The overall system presented allows the patient to sit closer in towards the slit lamp/tabletop assembly and the examining doctor for proper chin and forehead placement, thereby permitting proper, adequate, and comprehensive examinations that were previously very difficult with some obese and/or large-breasted patients.

Additionally, a freely positionable segmented arm is rotatably and pivotally attached to the underside of the tabletop upon which the slit lamp assembly is mounted. The pivotal connection allows the examining physician to tilt the entire table base top and the examining device assembly simultaneously to accommodate patients that are forced to sit in a hunched over position due to osteoporosis or other degenerative diseases.

The invention further comprises a plurality of removable and configurable elbow rest pads for use by the examining physician. The elbow rests comprise of a bean bag type construction made from a selection of a plurality of different materials and colors, wherein the bottom surface of the elbow rest pad comprises a rubberized or similar frictional gripping surface.

It should be understood that any one of the features of the invention may be used separately or in combination with other features. It should be understood that features which have not been mentioned herein may be used in combination with one or more of the features mentioned herein. Other systems, methods, features, and advantages of the present invention will be or become apparent to one with skill in the art upon examination of the drawings and detailed description. It is intended that all such additional systems, methods, features, and advantages be included within this description, be within the scope of the present invention, and be protected by the accompanying claims.

These and other objects, features and advantages of the present invention will be more readily apparent when considered in connection with the following, detailed description of preferred embodiments of the invention, which description is presented in conjunction with annexed drawings below.

BRIEF DESCRIPTION OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein. The components in the drawings are not necessarily to scale, emphasis instead being placed upon clearly illustrating the principles of the present invention. Moreover, in the drawings, like reference numerals designate corresponding parts throughout the several views.

The invention may take physical form in certain parts and arrangement of parts. For a more complete understanding of the present invention, and the advantages thereof, reference is now made to the following descriptions taken in conjunction with the accompanying drawings, in which.

DETAILED DESCRIPTION OF THE PREFERRED EMBODIMENT

The following discussion is presented to enable a person skilled in the art to make and use the invention. The general principles described herein may be applied to embodiments and applications other than those detailed below without departing from the spirit and scope of the present invention as defined by the appended claims. The present invention is not intended to be limited to the embodiments shown, but is to be accorded the widest scope consistent with the principles and features disclosed herein.

Figure 1:
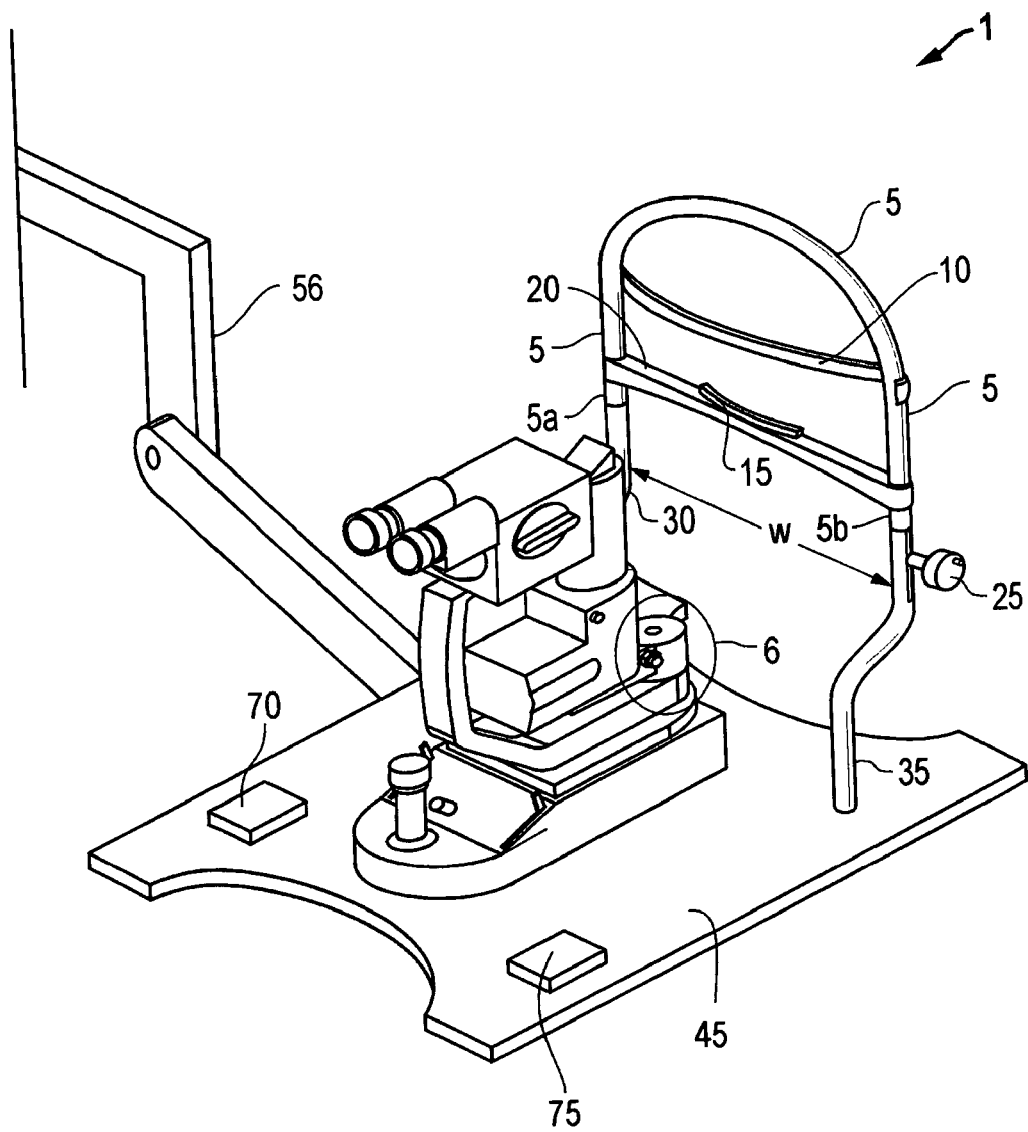
FIG. 1 is a perspective view of the modified slit lamp and head support frame assembly according to the present invention.

Referring now to the drawings, and particularly to FIG. 1, the chin/headrest assembly 1 for use with a modified slit lamp according to the present invention is shown. The preferred embodiment of the present invention comprises a modified slit lamp having a modified ocular and light source base assembly 6, a head support frame 5 having at least two upper vertically disposed leg members 5a, 5b, wherein leg members 5a and 5b are integrally connected to a substantially horizontal adjustable chin rest support bar member 20. The head support frame 5 structure is formed of a modular telescoping construction as is described below or can be constructed of a plurality of distinct, separate structure members connected to each other to achieve the same overall structure without departing from the scope and spirit of the present invention.

Frame 5 further comprises a substantially horizontal arcuate forehead supporting bracket member 10 removably interposed between the frame 5 and vertical support leg members 5a and 5b. Vertical support leg members 5a and 5b are connected by substantially horizontal support bar member 22. Lower vertically disposed support legs 30 and 35 provide foundational tie-in support to tabletop 45 for the overall structural stability of frame 5.

Adjustable chin rest support bar member 20 comprises an arcuate chin rest support 15 for ensuring proper position of a patient's head in the chin/headrest assembly 1. The chin rest support bar member 20 is constructed to so as to permit the physician to move the arcuate chin rest support 15 substantially vertically in a up and down movement along upper vertical disposed leg member 5a, 5b by rotatably adjusting chin rest support knob 25 located on at least vertical support leg 25. Knob 25 adjustably moves the chin rest support bar member 20 by means of a gear assembly mechanism as described below. Adjustable knob 25 can be positioned in a plurality of locations thereon assembly 1 without departing from the spirit of the invention. For example, knob 25 can be located on leg 5b as shown or on leg 5a in a similar manner.

FIG. 1 further depicts removable and configurable elbow rest pads 70, 75 of the present invention and depicts their preferred placement thereon table 45. Pads 70, 75 are provided for physician comfort due to the various positions that are provided by the pivotal tabletop 45 attached to arm 56. The top surface of pads 70, 75 are manufactured in a variety of colors and are constructed in a plurality of exterior materials including, but not limited to, cloth, leather, plastic, and vinyl or any other suitable material. The bottom of pads 70, 75 are constructed of a non-slip type material such as, but not limited to, rubber, Velcro®, plastic, and leather or other suitable non-slip material. The contents of pads 70, 75 for providing soft support include, but aren't limited to, small beans, small beaded Styrofoam® pellets, small beads, rice grains, and sand or any other similar suitable material. In the preferred embodiment, pads 70 and 75 are constructed in a rectangular fashion having a dimension of about 3 inches by 4 inches. However, pads 70 and 75 can be constructed in a plurality of geometric shapes including, but not limited to circles, squares, octagons, hexagons, triangles, and ovals without departing from the scope and spirit of the present invention.

Figure 1A:
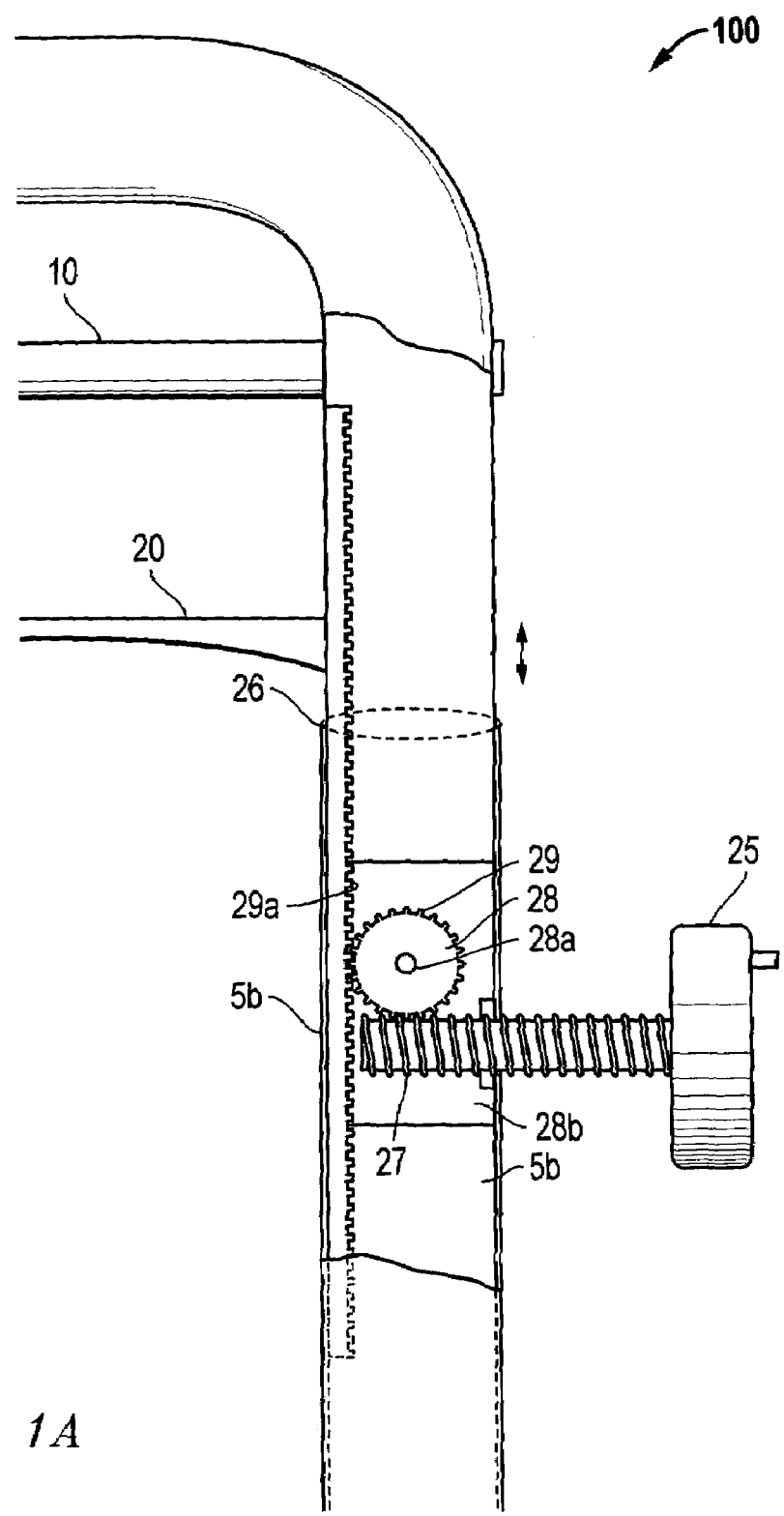
FIG. 1A is a cut-away view of the gear assembly mechanism for vertically adjusting a patient's head height according to the present invention.

In reference now to FIG. 1A, a cut-away view of the gear assembly 100 is shown. Gear assembly 100 comprises at least a vertically disposed gear running rail member 29a which is positionally secured via fasteners commonly known in the art to an interior wall of vertical leg member 5b. Upon gear running rail member 29a frictionally rotates a small tooth geared wheel 28, typically constructed of a nylon material but is not limited thereto, and having a plurality of teeth 29. The teeth 29 engage in the rail member 29a to cause an upper portion of frame 5 comprising vertical legs 5a and 5b to move up and down as described below.

Geared wheel 28 is removably connected to an interior wall of vertical leg member 5b via fastener 28a such as a threaded screw or the like. Geared wheel 28 itself is functionally positioned in rotatable alignment communication with the end of threaded shaft 27 disposed on knob 25. By the physician rotating knob 25 in a clockwise or counterclockwise direction the gear assembly mechanism 100 operationally functions to move the chin rest support bar 20 up and down. The entire upper portion of frame 5 comprising at least the chin rest 15 and the forehead supporting bracket member 10 is thereby guided throughout the up and down movement by the intermarriage of the telescoping design action of the vertical leg supports 5a, 5b which is permitted by the construction of frame 5.

The telescoping action is made possible by having a distinct stationary lower portion of support legs 5a and 5b which is connected to lower vertically disposed legs 30 and 35, respectively, and a distinct upper mobile portion wherein the upper mobile portion has a diameter slightly smaller than that of the lower portion of support legs 5a and 5b. Reference to FIG. 1A item number 26 depicts the general design to enable the telescoping action. Apart from the present invention's gear assembly 100, such bar telescoping action described functions similar to that found in most common telescoping products.

Figure 1B:
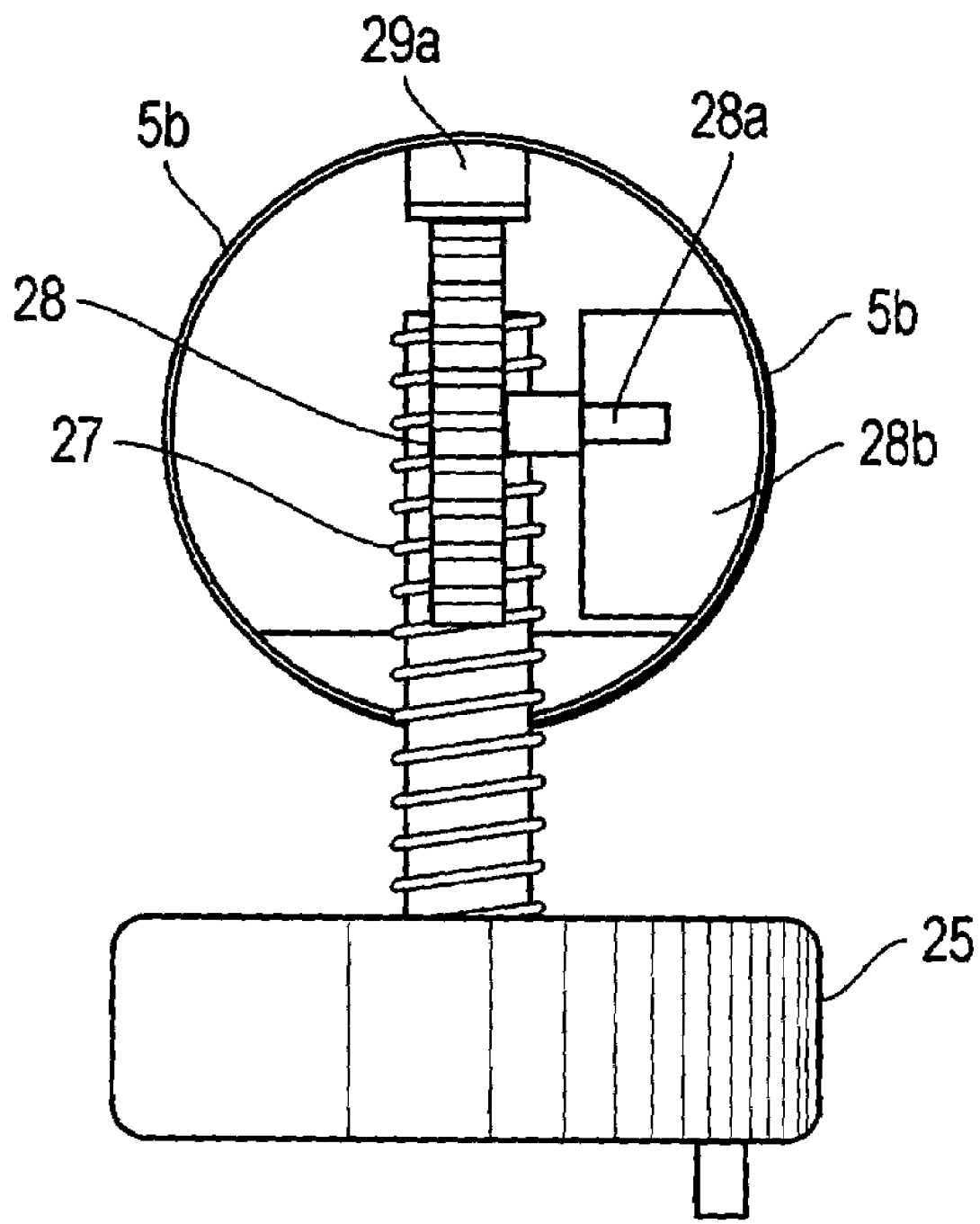
FIG. 1B is a cut-away view looking downward into the support frame from above the gear assembly mechanism depicting the gear assembly mechanism according to the present invention.

FIG. 1B provides further insight to the positional arrangement of the gear assembly mechanism 100 of FIG. 1A. In FIG. 1B is shown a cut-away downward looking view into leg 5b of frame 5 to depict the gear assembly mechanism 100 and its interactive component parts. Specifically shown for clarification is knob 25 having threaded shaft 27 disposed thereon such that geared wheel 28 is in positional and rotatable alignment therewith. In addition gear running rail member 29a is also shown in positional relationship geared wheel 28 for effectuating the up and down movement of legs 5a and 5b as described above. In addition, although shown in FIG. 1A, geared wheel 28 mounting block 28b is more clearly depicted in FIG. 1B. Geared wheel mounting block 28b is solely provided for mounting thereto geared wheel 28 via fastener 28a.

Vertical support legs 30, 35 and 5a, 5b of frame 5 are positioned on tabletop 45 in a substantially wider posture than is common in most slit lamp chin rest support devices and assemblies. Support legs 30 and 35 are removably attached at their individual bases to table 45 via common fasteners such as screws as is well known in the art. The present invention discloses vertical chin rest support legs 30, 35 and 5a, 5b that are spaced apart and having an interior distance, as measured between legs 30, 35, and 5a, 5b in the range of about 13 to 15 inches as depicted by the letter "w" in FIG. 1. The wider distance between legs 30, 35, and 5a, 5b provides for additional space to accommodate obese and/or large-breasted patients that are positioned at the slit lamp assembly for examination. In addition, legs 30 and 35 have been further designed to jut back or bend back and away in an arcuate fashion from a seated patient to create yet additional space for the obese and/or large-breasted patient and at the same time preventing the patient's upper body to encroach the slit lamp assembly. Such displacement of legs 30, 35 will be described in detail below in relation to FIG. 3.

Figure 2A:
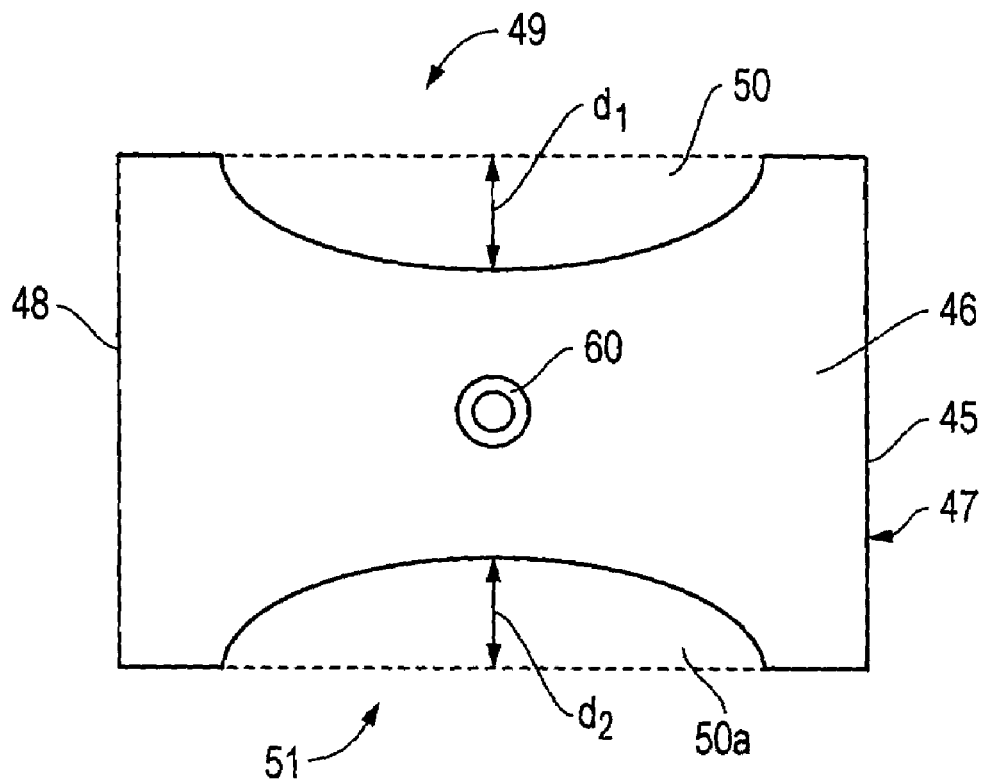
FIG. 2A is a bottom view of the pivotal table depicting curvilinear cut-outs in dotted lines according to the present invention.

FIG. 2A shows a view from the bottom side 46 of table 45, wherein two substantially curvilinear concave cut-outs 50, 50a are depicted for clarity. Table 45 comprises a substantially planar top (not shown in FIG. 2A), a substantially planar bottom 46, a substantially planar left side 48, a substantially planar right side 47, a physician's side 51, and a patient's side 49. Curvilinear concave cut-out 50 spans across the patient's side 49 of table 45 from about side 48 across the width of the patient's side 49 of table 45 to about side 47. Curvilinear concave cut-out 50a spans across the doctor's side 51 of table 45 from about side 48 across the width of doctor's side 51 of table 45 to about side 47. The apex of cut-out 50 extends away from the patient's side 49 inwardly on table 45 toward the center of table 45 at a distance of about one to three inches as depicted by the letter "$d_1$" in FIG. 2A. The apex of cut-out 50a extends away from the doctor's side 51 inwardly on table 45 toward the center of table 45 a distance of about one to three inches as depicted by letter "$d_2$" in FIG. 2A. It will be understood by those skilled in the art that the cut-out portion can be fashioned in a plurality of shapes without departing from the scope and spirit of the invention. Also shown is pivotable connection means 60 attached to the bottom 46 of table 45 which will be described in greater detail below.

Figure 2B:
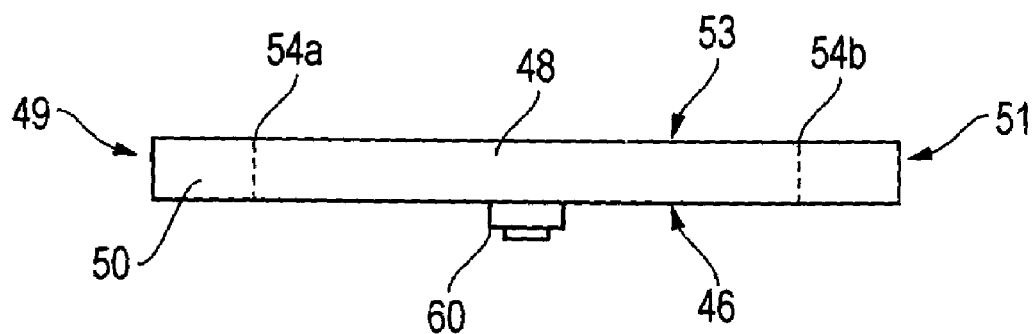
FIG. 2B is a right side view of the pivotal table depicting doctor's and patient's side cut-outs, according to the present invention.

FIG. 2B shows table 45 as viewed from side 48. Table 45 comprises a substantially planar top 53 which is substantially rectangular (without cut-outs $d_1$ and $d_2$) in overall shape, wherein sides 47 and 48 are shorter in length than sides 49 and 51. However, it should be understood that table 45 can be constructed in a plurality of exterior shapes without departing from the spirit of the invention provided a curvilinear cut-out 50 and 50a are constructed on the patient's side 49 and the doctor's side as described above.

A pivotable connection means 60 is removably and adjustably attached to the bottom 46 of the table 45 for attachment to a segmented area for positioning of table 45. The curvilinear cut-outs, 50 and 50a (not visible from the side view depicted) are indicated for reference by dashed lines 54a and 54b.

Figure 2C:
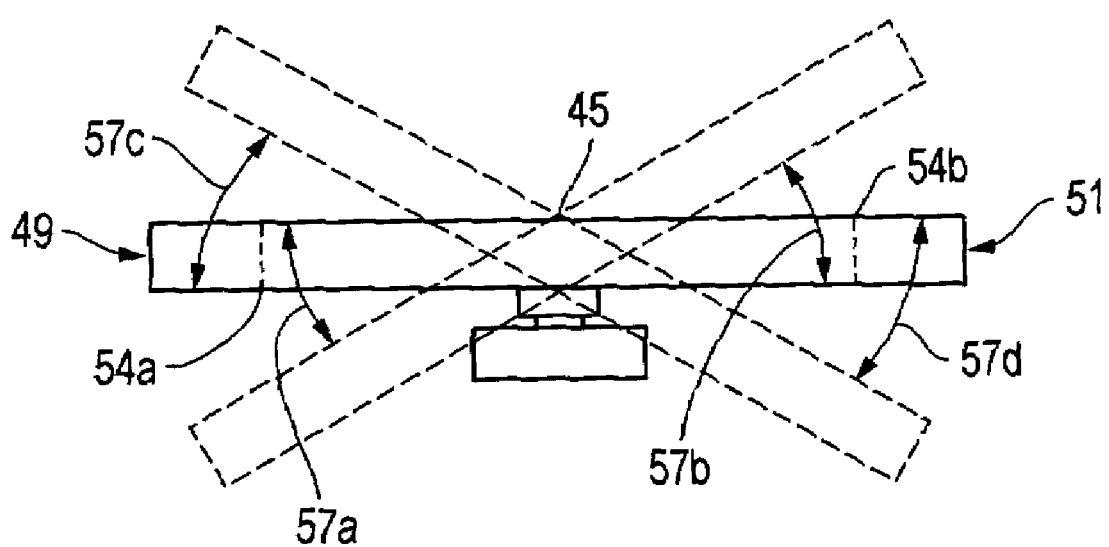
FIG. 2C is a side view depicting a range of positional views of the pivotal table with curvilinear cut-outs having a segmented arm attached from the right side according to the present invention.

FIG. 2C shows side view 47 of tabletop 45 and a side view portion of the segmented arm 56, wherein a substantial portion of the arm 56 is not shown so as to depict the plurality of angular planes of movement of table 45 and represented by example via arrows 57a, 57b, 57c, and 57d.

Figure 3:
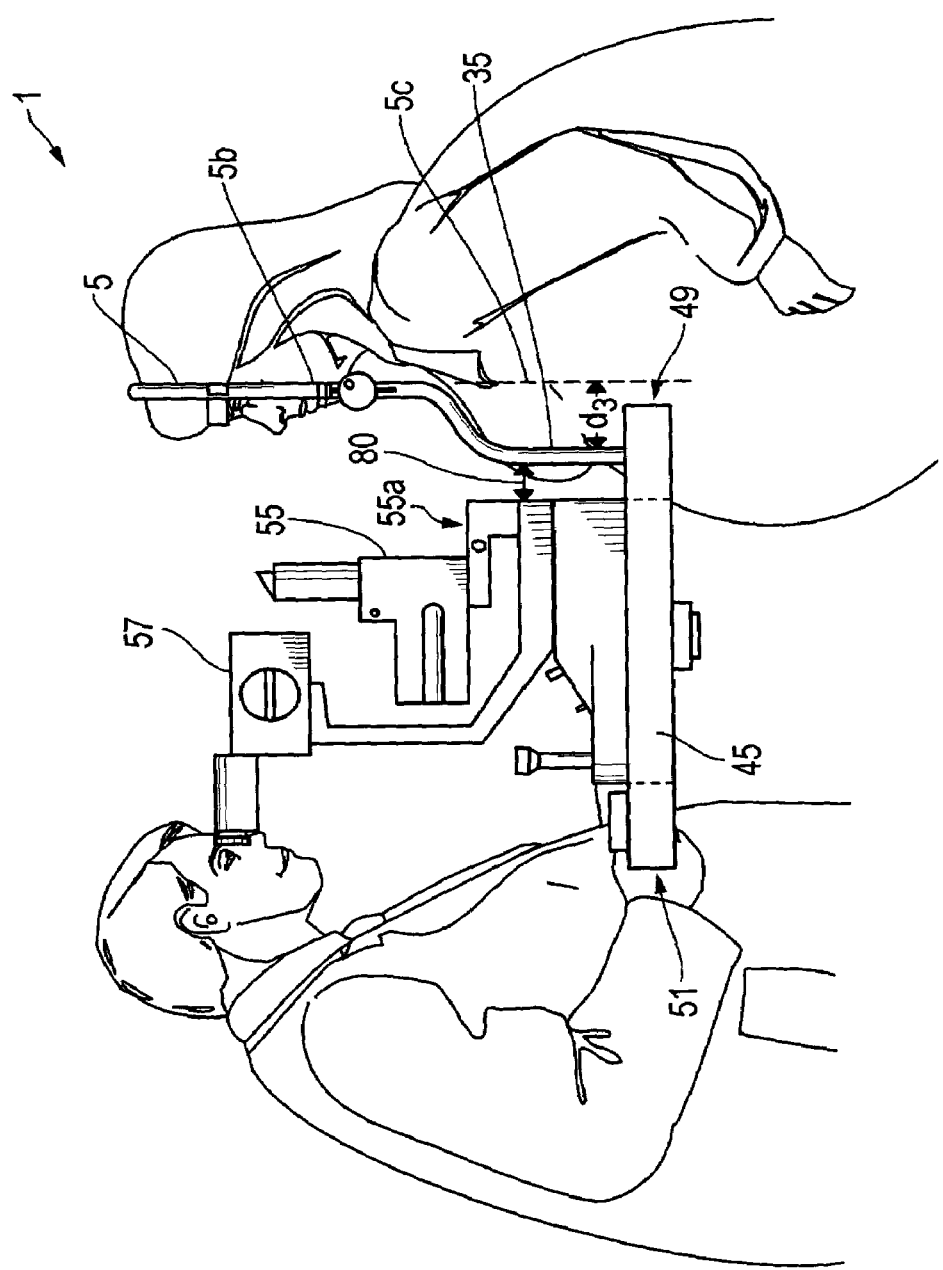
FIG. 3 is a side view of the overall modified slit lamp and chin/headrest assembly mounted on a modified tabletop according to the present invention.

FIG. 3 depicts a preferred embodiment of the modified slit lamp assembly 55 functionally positioned adjacent to the chin/headrest assembly 1 as described above and mounted thereto table 45. When connected to table 45 chin rest support legs 30 and 35 jut back and away in an arcuate fashion, at approximately a 90 degree angle although not limited thereto, from a seated patient being examined, thereby creating additional upper torso and chest space for the patient's comfort in the area of at least lower of legs 30 and 35 of assembly 1, thereby permitting ease of accommodation of assembly 1 and table 45 to obese and/or large-breasted women.

As mentioned above, and in further reference to FIG. 3, chin rest support legs 30 (not shown) and 35 are bent in an arcuate shape at approximately 90 degree angles. According to the present invention, the distance of "jut-back" or backward displacement (indicated by "$d_3$") of legs 30 and 35 towards the slit lamp examination assembly 55, is measured from an imaginary dropped vertical line 5c on the patient's side 49 from vertical leg 5a (not shown) and 5b. The amount of displacement "$d_3$" of bars 30, 35 from vertical line 5c is in the range of about two to four inches. To accommodate the displacement "$d_3$" of bars 30, 35 and to retain proper distance between the positioned patient's head and the oculars 57 of the slit lamp assembly 55, the patient's side 49 of the slit lamp light source base 55a of the slit lamp assembly 55 is shortened or stubbed off in the range of about ½ to 1½ inches as indicated by arrow 80.

In general reference now to FIGS. 1, 1A, 1B, 2A-2C, and 3, to examine an obese, large-breasted, and/or patient suffering from degenerative back diseases utilizing the present invention the following steps are taken. First, the physician seats the patient, in a substantially vertical position, in an examination chair. Next, the physician positions the examination assembly 1 mounted on table 45 into a proper position to effectuate proper and adequate examination of the patient's eyes. In this step, the physician adjusts the table's 45 position angle, relative to the patient's posture, to allow those with poor postures and/or degenerative back disorders to be fully examined as was not possible prior to the present invention.

Furthermore, the present invention utilizes the combination of the slit lamp assembly 55, the head/chin rest combination 5, 10, 15 and a segmented arm 56 connected to a pivotal connection means 60 on the table's 45 bottom side 46, wherein the table 45 has a plurality of physique accommodating cut-outs 50, 50a to assist in accomplishing a comprehensive examination. Next, the physician positions the patient's chin in a chin rest 15 and adjusts the height of the patient's head up and down in the chin rest 15 by rotating an adjustment knob 25 located on the vertical leg(s) 5 and/or 5a of frame 5. The up and down positioning of the head allows the physician to properly position the patient's head against the forehead rest and their eyes in front of the slit lamp assembly 55 for examination. At this point the physician can commence with proper and comprehensive examination of the patient's eyes regardless of obesity or degenerative back disorders.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

The invention claimed is:

1. An ophthalmic examination system, the system comprising:
    an eye examination assembly;
    a head support structure and a chin support structure, wherein the support structures comprise at least one arcuately disposed structural member portion, the arcuately disposed portion providing a set-back region for accommodating a patient's body positioning relative to the eye examination assembly;
    a support table having a plurality of cut-outs, wherein the eye examination assembly and the support structures are attached to the table, wherein a patient's body can be cooperatively positioned in a functional relationship with the table and the plurality of cut-outs thereof, wherein one of the plurality of cut-outs has an apex that extends away from a patient's side of the table inwardly toward a center of the table; and
    wherein the combination of the eye examination assembly, the support structures and the table permit a plurality of patient and doctor physiques and postures to be accommodated for examination, thereby facilitating comprehensive eye care to at least obese, large-breasted patients, and/or patients with degenerative back disease patients.

2. The system of claim 1 wherein the plurality of cut-outs are curvilinear in shape.

3. The system of claim 1 wherein the apex of the plurality of cut-outs of the support table extends into the center of the table in the range of about 1 to 3 inches.

4. The system of claim 3 wherein a cut-out exists on the doctor's side of the table.

5. The system of claim 3 wherein a cut-out exists on the patient's side of the table.

6. The system of claim 3 wherein the support table further comprises a pivotal connection disposed thereon a bottom side.

7. The system of claim 6 further comprising a modular segmented arm removably attached to the pivotal connection, wherein a user can discretely position the arm and table combination to achieve desired positional arrangement with a patient.

8. The system of claim 1 wherein the eye examination assembly comprises a light source base member, wherein the base member is shortened to accommodate at least a lower portion of the support structures.

9. The system of claim 8 wherein the base member is shortened in the range of about ½ inch to 1½ inches.

10. The system of claim 1 wherein the support structure for accommodating proper patient head and upper torso positioning provides an area having a width of about 13 to 15 inches.

11. The system of claim 10 wherein the head and chin support structure for accommodating proper patient positioning further provides at least one arcuately disposed structural member portion comprising a set-back region having a set-back depth range of about two to four inches, wherein the set-back region is accomplished by a plurality of approximate 90 degree arcuate bends in the support structures.

12. The system of claim 1 wherein the chin support structure comprises an adjustable chin rest bar member, wherein the chin support structure is adjustable up and down by way of a rotatably adjustable knob and gear assembly mechanism, wherein the knob is functionally connected to a gear assembly for raising and lowering at least an upper portion of the chin and head support structures.

13. The system of claim 1 wherein the eye examination assembly is a slit lamp.

14. The system of claim 1 wherein the support table further comprises plurality of configurable elbow rest pads removably positioned on the table, wherein the pads are rectangular in shape having a dimension of about 3 inches by 4 inches.

15. The system of claim 14 wherein the elbow rest pads are constructed in a plurality of geometric shapes selected from the group consisting of circles, squares, octagons, hexagons, triangles, and ovals.

16. The system of claim 14 wherein a top portion of the elbow rest pads are constructed from materials selected from the group consisting of cloth, leather, plastic and vinyl.

17. The system of claim 16 wherein the top portion of the pads are manufactured in a plurality of colors.

18. The system of claim 16 wherein a bottom portion of the pads are constructed from a non-slip material.

19. The system of claim 18 wherein the non-slip material is selected from the group consisting of rubber, plastic, and leather.

20. The system of claim 14 wherein the contents of the pads are selected from the group consisting of small beans, small beads, rice grains, and sand.

21. A method for positioning patients with various body proportions and muscular development for eye examination, the method comprising the steps of:

seating a patient in an examination chair;

positioning an apparatus comprising a chin support, a head support bracket and an eye examination assembly such that the apparatus is positioned into operational arrangement with a patient's head, wherein the assembly is mounted to a table pivotally connected to a support arm, wherein the combination of a pivotal connection and the arm permit a plurality of discrete positional examination angles to be achieved, and the pivotal connection allows an examining physician to tilt the table through a plurality of angular planes;

positioning the patient's chin on an adjustable support;

adjusting the adjustable support so as to cause the patient's forehead to come into proper engagement with a forehead supporting bracket, thereby permitting a physician to comprehensively examine a wide range of patient body structures, wherein the patient is obese and/or large-breasted; and, examining the patient's eyes.

* * * * *